(12) United States Patent
Sasaki (10) Patent No.: US 10,451,574 B2
(45) Date of Patent: Oct. 22, 2019

(54) INSPECTING METHOD FOR HEATSINK AND MANUFACTURING METHOD FOR HEATSINK (71) Applicant: TOYOTA JIDOSHA KABUSHIKI KAISHA, Toyota-shi (JP)

(72) Inventor: Kazuyuki Sasaki, Nagoya (JP)

(73) Assignee: TOYOTA JIDOSHA KABUSHIKI KAISHA, Toyota-shi (JP)

(*) Notice: Subject to any disclaimer, the term of this patent is extended or adjusted under 35 U.S.C. 154(b) by 189 days.

(21) Appl. No.: 15/782,895

(22) Filed: Oct. 13, 2017

(65) Prior Publication Data

US 2018/0106741 A1 Apr. 19, 2018

(30) Foreign Application Priority Data

Oct. 19, 2016 (JP) .................. 2016-205153

(51) Int. Cl.
*G01N 25/72* (2006.01)
*G01J 5/08* (2006.01)
*B22D 19/08* (2006.01)
*H01L 23/36* (2006.01)

(52) U.S. Cl.
CPC ............ *G01N 25/72* (2013.01); *B22D 19/08* (2013.01); *G01J 5/0806* (2013.01); *H01L 23/36* (2013.01)

(58) Field of Classification Search
CPC ..................................................... G01N 25/72
See application file for complete search history.

(56) References Cited

U.S. PATENT DOCUMENTS 6,915,069 B2 * 7/2005 Bradenbaugh ............ G01J 5/00
374/E1.021
9,519,844 B1 * 12/2016 Thompson ........... G06K 9/6267

FOREIGN PATENT DOCUMENTS

| JP | 57-202683 | 12/1982 | |
| JP | 2004363310 A * | 12/2004 | ............... C09K 5/00 |
| JP | 2010025762 A * | 2/2010 | |
| JP | 2013247328 A * | 12/2013 | |

* cited by examiner

*Primary Examiner* — Clayton E. LaBalle
*Assistant Examiner* — Leon W Rhodes, Jr.
(74) *Attorney, Agent, or Firm* — Oblon, McClelland, Maier & Neustadt, L.L.P.

(57) ABSTRACT

An inspection method for a heatsink according to the present disclosure includes a measurement preparation step of placing the heatsink in a place where radiated-heat quantities can be measured by first and second thermal sensors, each of the first and second thermal sensors including a temperature sensor and a heat-concentrating mirror with a heat-receiving surface curved in a concave shape, the first and second thermal sensors being disposed in different places in a state where a heat-receiving line is inclined from a direction in which the fin protrudes by a predetermined angle, a measurement step of acquiring first and second radiated-heat quantities from the first and second thermal sensors, respectively, and a determination step of determining that a coating state of the coating is fine when a total value of the first and second radiated-heat quantities is larger than a predetermined range defined in advance.

9 Claims, 9 Drawing Sheets

INSPECTING METHOD FOR HEATSINK AND MANUFACTURING METHOD FOR HEATSINK

CROSS REFERENCE TO RELATED APPLICATIONS

This application is based upon and claims the benefit of priority from Japanese patent application No. 2016-205153, filed on Oct. 19, 2016, the disclosure of which is incorporated herein in its entirety by reference.

BACKGROUND

The present disclosure relates to a heatsink. For example, the present disclosure relates to an inspecting method and a manufacturing method for a heatsink coated with a coating for improving a heat radiation property of the heatsink.

The heat radiation capability of heatsinks is improved by providing them with fins protruding from their base parts, which come into contact with heat-generating elements, and thereby increasing areas from which heat is radiated. Further, in recent years, the heat radiation capability per volume of a heatsink is improved by coating its fins with a coating for accelerating heat radiation (e.g., resin paint). Therefore, Japanese Unexamined Patent Application Publication No. S57-202683 discloses an example of a method for inspecting a coating radiated-heat quantity to a heatsink.

Japanese Unexamined Patent Application Publication No. S57-202683 relates to a manufacturing method for a heat radiation base for an electric heating apparatus. In the manufacturing method of a heat radiation base for an electric heating apparatus disclosed in Japanese Unexamined Patent Application Publication No. S57-202683, when a base body that serves as a basis for the heat radiation base is fox by die-casting and a resin coating layer is formed on a heat-radiating surface of this base body by resin injection molding using a metal mold, the aforementioned resin injection molding is performed by incorporating the aforementioned base body into the aforementioned metal mold in a high-temperature state immediately after the molding of the aforementioned base body by the die-casting.

SUMMARY

The present inventors have found the following problem. When a coating is formed as described above, it is necessary to inspect whether the coating is properly formed. For this inspection method, it is concealable to perform a visual inspection, an inspection using a thermography, an inspection in which a quantity of heat radiated from the heatsink (hereinafter referred to as a "radiated-heat quantity" from the heatsink) is measured by using a thermal sensor, or the like. However, in the case of the visual inspection, there is a problem that it is difficult to visually check whether the coating is properly formed on the side walls of the fins. The inspection using a thermography is a measurement method in which the resolution of the thermography is determined according to the number of pixels thereof. Therefore, there is a problem that when the resolution of the measurement is increased, the number of pixels to be processed is increased, thus increasing the inspection time. In addition, there is a problem that the cost for the apparatus increases according to the resolution in the inspection using a thermography. In the inspection in which a radiated-heat quantity from the heatsink is measured by using a thermal sensor, the radiated-heat quantity from the heatsink is measured by measuring heat rays (infrared rays) emitted from a predetermined area by using a temperature sensor equipped with a light-concentrating mirror or the like. However, since the heat-radiating surface of the heatsink has a non-planar shape, heat rays (infrared rays) are emitted in a scattered manner (i.e., in various directions), thus causing a problem that measurement of all the side walls (or the entire side wall) of the heatsink cannot be accurately performed. That is, there is a problem that a formation state of a coating cannot be accurately inspected by using any of the ordinarily conceivable inspection methods.

The present disclosure has been made in view of the above-described circumstances and an object thereof is to accurately measure a formation state of a coating formed in a heatsink.

A first exemplary aspect is an inspection method for a heatsink including a base part and a fin disposed in the base part so as to protrude therefrom, the base part being a part that comes into contact with a heat-generating element, the fin being coated with a coating, the inspection method including: a measurement preparation step of placing the heatsink in a place where radiated-heat quantities can be measured by first and second thermal sensors, each of the first and second thermal sensors including a temperature sensor and a heat-concentrating mirror with a heat-receiving surface curved in a concave shape, the heat-concentrating mirror being configured to concentrate received heat onto the temperature sensor based on the concave shape, the first and second thermal sensors being disposed in different places in a state where a center line connecting a bottom of the concave shape of the heat-receiving surface with the temperature sensor is inclined from a direction in which the fin protrudes by a predetermined angle; a measurement step of measuring the radiated-heat quantity of the fin and acquiring first and second radiated-heat quantities from the first and second thermal sensors, respectively; and a determination step of determining that a coating state of the coating is fine when a total value of the first and second radiated-heat quantities is larger than a predetermined range defined in advance.

According to the above-described aspect, it is possible to improve accuracy of a pass/fail determination on a formation state of a coating formed on side walls of a fin provided in a heatsink by measuring radiated-heat quantities of different side surfaces of the fin by a plurality of temperature sensors disposed in places where the side surfaces of the fin are exposed and determining pass/fail of the formation state of the coating based on the total value of the plurality of measured radiated-heat quantities.

In another aspect, in the inspection method for a heatsink, the first and second thermal sensors are disposed in places where exposed areas of the fin that can be observed from the thermal sensors are equal to each other, and the determination step further includes a coating unevenness determination step of determining that a coating state of the coating is defective when a difference between the first and second radiated-heat quantities has a value outside a predefined coating unevenness determination range.

According to the above-described another aspect, by performing the pass/fail determination of a heatsink based on presence/absence of coating unevenness, it is unnecessary to perform complicated calculation, thus making it possible to reduce the inspection time.

In another aspect, in the inspection method for a heatsink, the fin is formed so as to protrude in a vertical direction with respect to the base part, the first and second thermal sensors are arranged in left-right symmetrical places with respect to a center line of the heatsink, the center line being defined in the vertical direction with respect to the base part of the heatsink, and the determination step further includes a coating unevenness determination step of determining that a coating state of the coating is defective when a difference between the first and second radiated-heat quantities has a value outside a predefined coating unevenness determination range.

According to the above-described another aspect, since the pass/fail determination of a heatsink is made based on presence/absence of coating unevenness, there is no need to perform complicated calculation, thus making it possible to reduce the inspection time.

In another aspect, in the inspection method for a heatsink, the predetermined angle is an angle at which an area of the side surface of the fin that is exposed to the heat-receiving surface is maximized.

According to the above-described another aspect, since the inspection can be performed based on a quantity of heat (hereinafter referred to as a "heat quantity") emitted from the maximum observable area of the side wall of the fin, the inspection accuracy can be further improved.

In another aspect, in the inspection method for a heatsink, each of the heat-receiving surfaces of the first and second thermal sensors have an area that can collectively receive heat rays (infrared rays) emitted from all the fins provided in the heatsink.

According to the above-described another aspect, since the radiated-heat quantities of all the fins can be acquired without scanning the measurement place, the inspection time can be reduced.

In another aspect, in the inspection method for a heatsink, the first thermal sensor includes a heat-shield plate disposed in front of the heat-receiving surface, the heat-shield plate being configured to restrict an area on the heat-receiving surface on which heat rays (infrared rays) are incident to a predetermined area, and the inspection method further includes a partial measurement step of measuring the third radiated-heat quantity in a state where the heat-shield plate is disposed in front of the first thermal sensor, and a constant calculation step of calculating a constant from the third radiated-heat quantity, the constant being used to define the predetermined range.

According to the above-described another aspect, even when the absolute value of the temperature of the fin is unknown at the point when the radiated-heat quantity of the fin is measured, it is possible to determine the predetermined range used for the pass/fail determination based on the temperature of the fin and thereby to perform the pass/fail determination.

In another aspect, the inspection method for a heatsink further includes an overheating step of overheating the heatsink by using a heater, the heat being configured to raise the temperature of the heatsink to a predefined measurement temperature before the measurement step, and a constant calculation step of calculating a constant from the measurement temperature, the constant being used to define the predetermined range used in the determination step.

According to the above-described another aspect, since the temperature of the fin at the point when the radiated-heat quantity is measured is known, the pass/fail determination can be swiftly performed without estimating the temperature of the fin.

Another exemplary aspect is a manufacturing method for a heatsink, including: a housing formation step of manufacturing a heatsink housing by casting, the heatsink housing including a base part and a fin disposed in the base part so as to protrude therefrom, the base part being a part that comes into contact with a heat-generating element; a film formation step of forming a heatsink by coating a surface of the heatsink housing with a coating so that at least the fin is covered by the coating; a measurement preparation step of placing the heatsink housing, which has undergone the film formation step, in a place where radiated-heat quantities can be measured by first and second thermal sensors, each of the first and second thermal sensors including a temperature sensor and a heat-concentrating mirror with a heat-receiving surface curved in a concave shape, the heat-concentrating mirror being configured to concentrate received heat onto the temperature sensor based on the concave shape, the first and second thermal sensors being disposed in different places in a state where a center line connecting a bottom of the concave shape of the heat-receiving surface with the temperature sensor is inclined from a direction in which the fin protrudes by a predetermined angle; a measurement step of measuring the radiated-heat quantity of the fin and acquiring first and second radiated-heat quantities measured by the first and second thermal sensors, respectively; and a determination step of determining that a coating state of the coating is fine when a total value of the first and second radiated-heat quantities is larger than a predetermined range defined in advance.

According to the above-described aspect, it is possible to improve accuracy of a pass/fail determination on a formation state of a coating formed on side walls of a fin provided in a heatsink by measuring radiated-heat quantities of different side surfaces of the fin by a plurality of temperature sensors disposed in places where the side surfaces of the fin are exposed and determining pass/fail of the formation state of the coating based on the total value of the plurality of measured radiated-heat quantities, and thereby to reduce the defective ratio of heatsinks.

In another aspect, in the inspection method for a heatsink, the film formation step, the measurement preparation step, and the measurement step are performed before the temperature of the heatsink housing that has been raised by the casting performed in the housing formation step is lowered to or below a predefined measurement-performable temperature.

According to the above-described aspect, it is possible to omit the step of overheating a heatsink for the inspection of the heatsink and thereby to reduce the time required for the manufacturing process.

According to the inspection method and the manufacturing method for a heatsink in accordance with the present disclosure, it is possible to accurately measure a formation state of a coating formed in a heatsink.

The above and other objects, features and advantages of the present invention will become more fully understood from the detailed description given hereinbelow and the accompanying drawings which are given by way of illustration only, and thus are not to be considered as limiting the present invention.

DESCRIPTION OF EMBODIMENTS

First Embodiment

Embodiments according to the present disclosure are hereinafter explained with reference to the drawings. For clarifying the explanation, the following descriptions and the attached drawings are partially omitted and simplified as appropriate. Note that the same symbols are assigned to the same components throughout the drawings and duplicated explanations are omitted as required.

Figure 1:
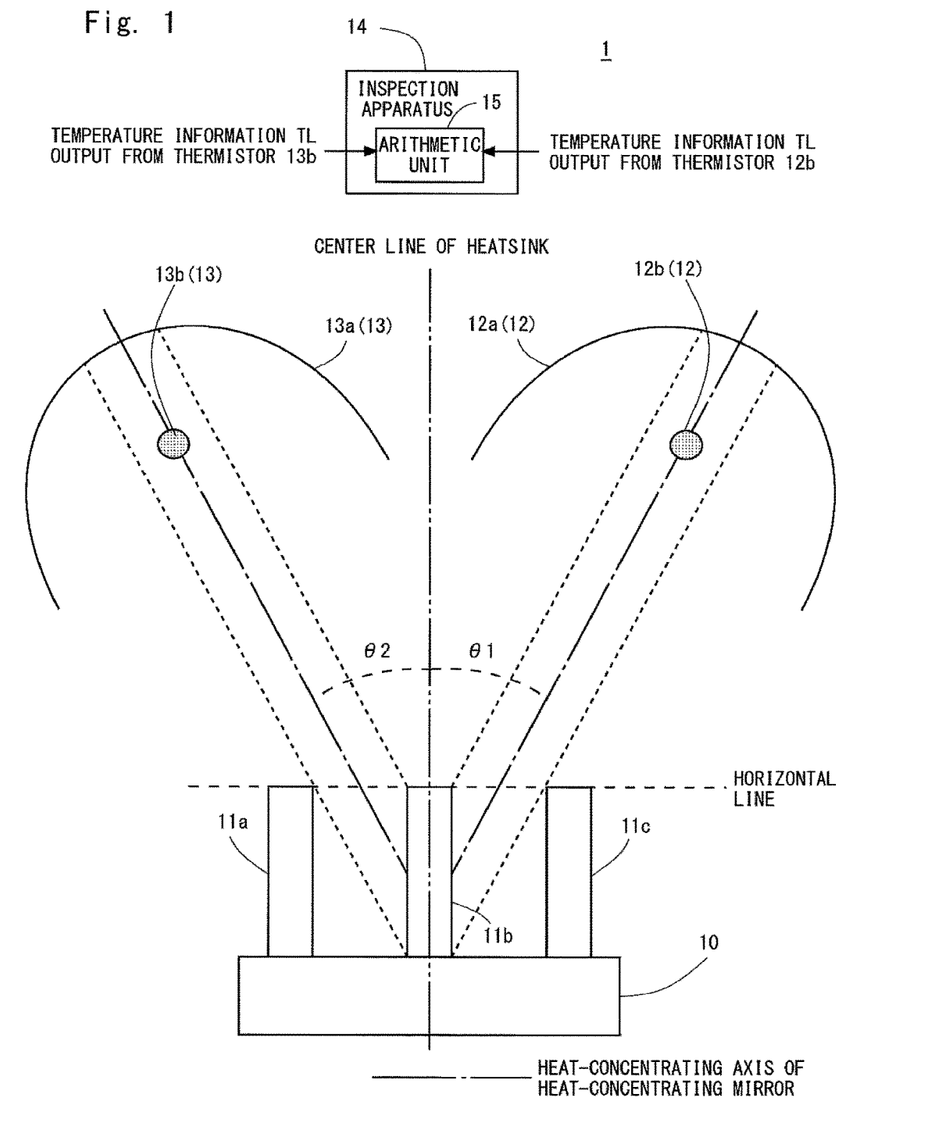
FIG. 1 is a schematic diagram for explaining a configuration of a coating inspection system according to a first embodiment.

Firstly, FIG. 1 shows a schematic diagram of a configuration of a coating inspection system 1 according to a first embodiment. In the example shown in FIG. 1, a heatsink is formed by a base part 10 and fins 11a to 11c. For example, this heatsink is formed by casting. Further, though it is omitted in FIG. 1, the heatsink is coated with a coating so that at least fins 11a to 11c are covered by the coating. This coating is, for example, resin paint and has an effect of accelerating radiation of heat from the heatsink. Further, in the following explanation, a component formed by the base part 10 and the fins 11a to 11c is referred to as a "heatsink housing". Meanwhile, a component that is obtained by forming a coating on the fins 11a to 11c is referred to as a "heatsink".

Further, the base part 10 is a part that comes into contact with a heat-generating element. The fins 11a to 11c are provided in the base part 10 so as to protrude therefrom. The direction in which the fins 11a to 11c protrude is a direction vertical (i.e., perpendicular) to a heat-radiating surface disposed in a place opposed to a contact surface of the base part 10, which is one of the surfaces of the base part 10 that comes into contact with the heat-generating element. Note that although the heatsink is fixed, for example, by using a fixing jig or the like so that a positional relation between the heatsink and thermal sensors (which are described later) is kept unchanged when measurement is performed, the jig is omitted in FIG. 1.

Further, as shown in FIG. 1, in the coating inspection system 1 according to the first embodiment, a first thermal sensor (e.g., a thermal sensor 12) and a second thermal sensor (e.g., a thermal sensor 13) are provided for one heatsink. The thermal sensor 12 includes a heat-concentrating mirror 12a and a thermistor 12b. The thermal sensor 13 includes a heat-concentrating mirror 13a and a thermistor 13b. Each of the heat-concentrating mirrors 12a and 13a has a heat-receiving surface curved in a concave shape and concentrates received heat onto the thermal sensor (e.g., thermistor) based on the concave shape (i.e., by the concave shape). Each of the thermistors 12b and 13b outputs temperature information having a value that changes according to the temperature that is raised based on heat rays (i.e., by heat rays (infrared rays)) that are directly incident on the thermistor and heat rays (infrared rays) that are concentrated by the heat-concentrating mirror. This temperature information is transmitted to an arithmetic unit 15 of an inspection apparatus 14. The inspection apparatus 14 shows an inspection result and information about the progress of the inspection to a user and controls the inspection flow. The arithmetic unit 15 performs necessary calculation and determination in the inspection. In the example shown in FIG. 1, temperature information TR output from the thermistor 12b and temperature information TL output from the thermistor 13b are supplied to the arithmetic unit 15.

Further, in the coating inspection system 1 according to the first embodiment, the thermal sensors 12 and 13 are disposed in different places in a state where a heat-receiving axis connecting the bottom of the concave shape of the heat-receiving surface with the temperature sensor is inclined from the direction in which the fins 11a to 11c protrude by a predetermined angle. More specifically, the thermal sensors 12 and 13 are disposed in places from which side surfaces of the fin can be viewed and in which exposed areas of the fin that can be observed from the thermal sensors are equal to each other. In the example shown in FIG. 1, the thermal sensors 12 and 13 are arranged in left-right symmetrical places with respect to the center line of the heatsink defined in the vertical direction with respect to the base part of the heatsink. That is, in the example shown in FIG. 1, the thermal sensors 12 and 13 are arranged so that an inclination $\theta 1$ of the heat-concentrating axis of the thermal sensor 12 from the center line of the heatsink is equal to an inclination $\theta 2$ of the heat-concentrating axis of the thermal sensor 13 from the center line of the heatsink. Further, in the example shown in FIG. 1, the thermal sensor 12 measures a radiated-heat quantity from the right-side surface of the fin and the thermal sensor 13 measures a radiated-heat quantity from the left-side surface of the fin.

Note that in the example shown in FIG. 1, since the direction in which the fins protrude is the same as the direction in which the center line of the heatsink extends, each of the inclinations $\theta 1$ and $\theta 2$ is the above-described predetermined angle. Further, in the coating inspection system 1 according to the first embodiment, each of the inclinations $\theta 1$ and $\theta 2$ is set to an angle at which an area of the side surface of the fin that is exposed to the heat-receiving surface (e.g., the heat-concentrating mirror) of the thermal sensor is maximized. In the example shown in FIG. 1, each of the inclinations $\theta 1$ and $\theta 2$ is set so that the side surface of the fin extending from the bottom of the fin to the top thereof is exposed to the heat-concentrating mirror. By disposing the thermal sensors 12 and 13 so that wider areas of the fin are exposed to the thermal sensors as described above, the thermal sensors 12 and 13 can acquire heat rays (infrared rays) from wider areas. As a result, in the coating inspection system 1 according to the first embodiment, it is possible to increase the area of the side surface of the fin to be inspected and thereby to improve the inspection accuracy.

Figure 2:
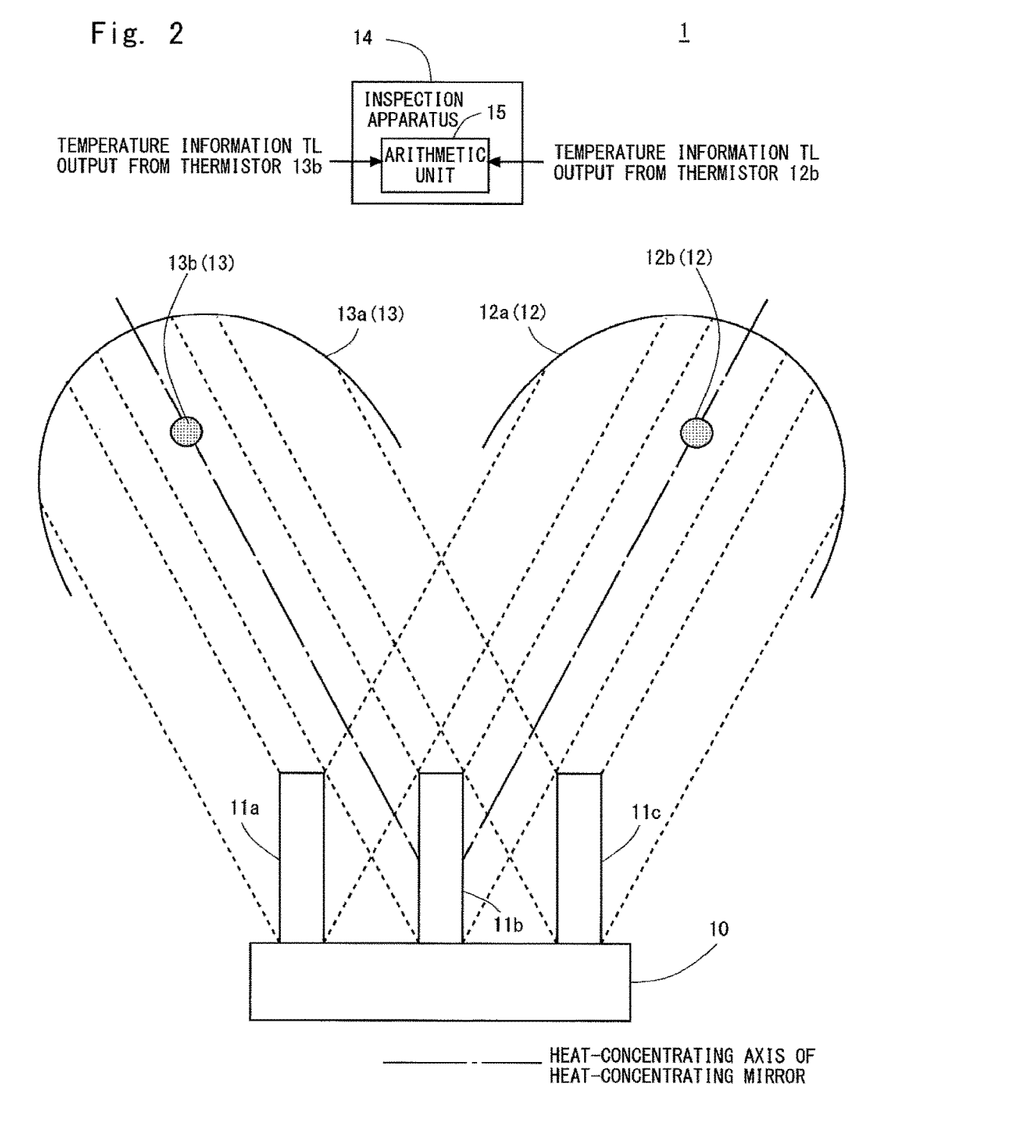
FIG. 2 is a diagram for explaining a size of a heat-concentrating mirror according to the first embodiment.

Next, FIG. 2 shows a diagram for explaining a size of the heat-concentrating mirror according to the first embodiment. As shown in FIG. 2, each of the heat-concentrating mirrors 12a and 13a according to the first embodiment has an area that can collectively receive heat rays (infrared rays) radiated from all the fins provided in the heatsink. As a result, in the coating inspection system 1 according to the first embodiment, it is possible to acquire the radiated-heat quantities of all the fins without scanning the measurement place and thereby to reduce the inspection time.

Figure 3:
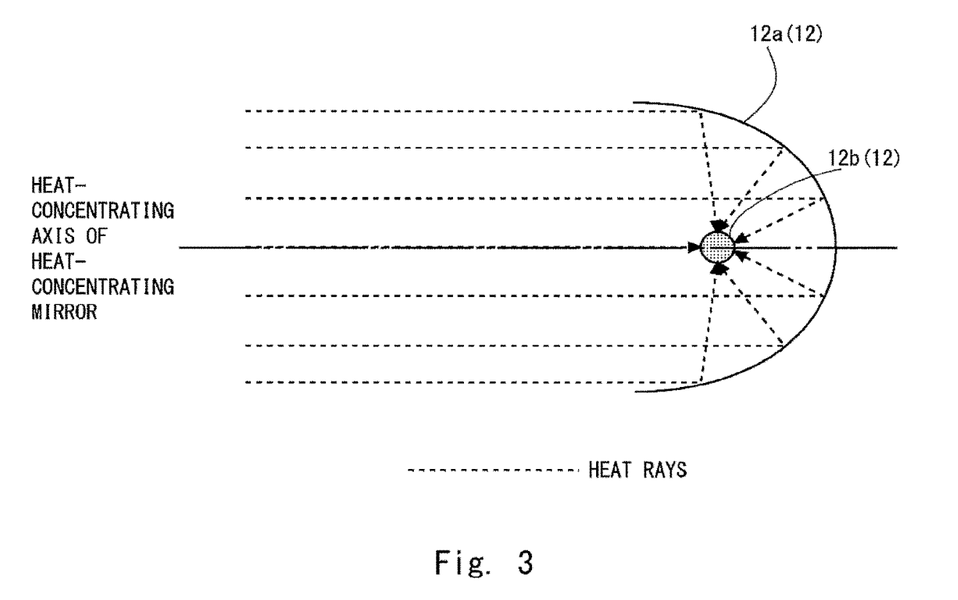
FIG. 3 is a diagram for explaining a heat-concentrated state in a thermal sensor according to the first embodiment.

Next, FIG. 3 shows a diagram for explaining a heat-concentrated state in the thermal sensor according to the first embodiment. As shown in FIG. 3, the heat-receiving surface of the heat-concentrating mirror has a curvature with which the heat-receiving surface can concentrate heat rays (infrared rays) that travel in parallel with the heat-concentrating axis and incident on the heat-receiving surface onto the thermistor. For example, for this curvature, a parabolic shape or the like can be used. As a result, in the coating inspection system 1 according to the first embodiment, it is possible to reduce the effect caused by causes other than the heat rays (infrared rays) that travel in parallel with the heat-concentrating axis and incident on the heat-receiving surface and thereby to acquire a radiated-heat quantity in proportion to the area of the side wall of the fin exposed to the heat-concentrating mirror.

Figure 4:
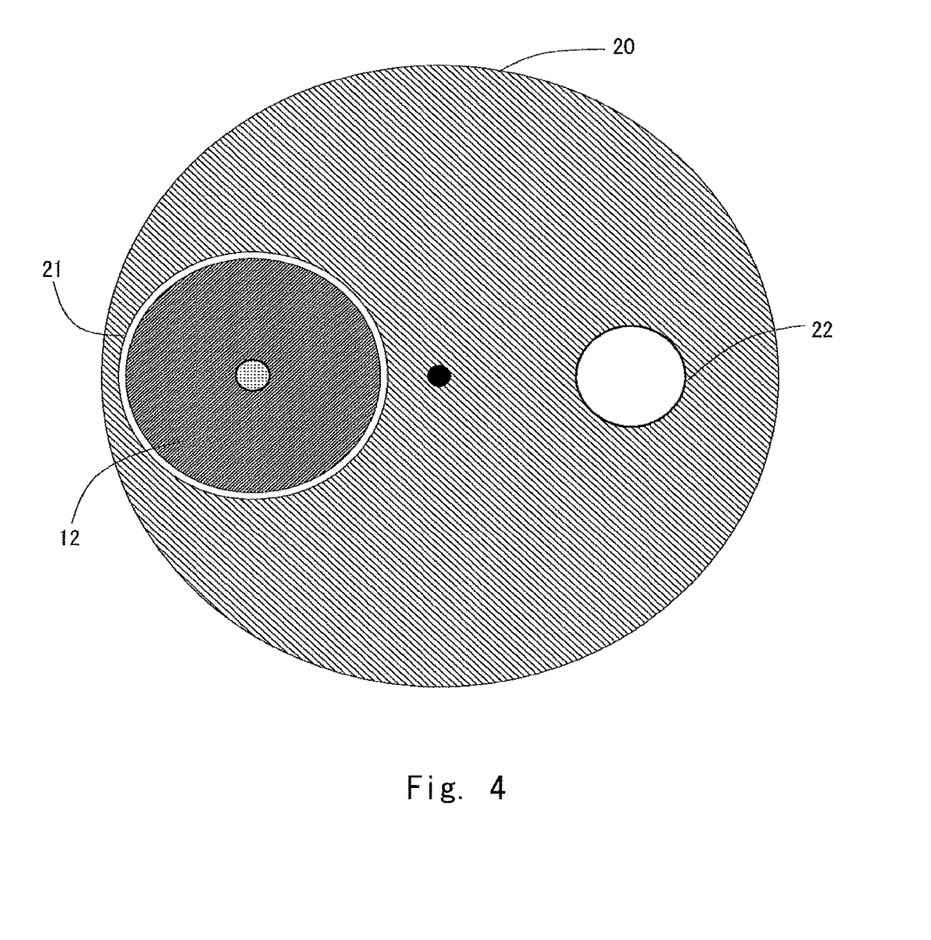
FIG. 4 is a diagram for explaining a configuration of a rotation plate attached to the thermal sensor according to the first embodiment.

Next, FIG. 4 shows a diagram for explaining a configuration of a rotation plate attached to the thermal sensor according to the first embodiment. In the coating inspection system 1 according to the first embodiment, in order to measure the temperature of the fin, the temperature is measured by using one of the thermal sensors while restricting heat rays (infrared rays) that are incident on the other thermal sensor. To perform this restriction on the quantity of received heat, a rotation plate with openings having different sizes formed therein is provided in one of the thermal sensors 12 and 13. In the coating inspection system 1 according to the first embodiment, the rotation plate is provided in the thermal sensor 12. In the example shown in FIG. 4, a rotation plate 20 is provided for the thermal sensor 12. This rotation plate 20 is disposed in front of the thermal sensor 12. The rotation plate 20 has a complete opening 21 and a partial opening (or a small opening) 22. When the complete opening 21 is located in front of the thermal sensor 12, heat rays (infrared rays) are incident on the entire heat-receiving surface of the thermal sensor 12. In contrast, when the partial opening 22 is located in front of the thermal sensor 12, a part of the rotation plate 20 other than the partial opening 22 serves as a heat-shield plate and hence heat rays (infrared rays) that are incident on the heat-receiving surface of the thermal sensor 12 are restricted.

Figure 5:
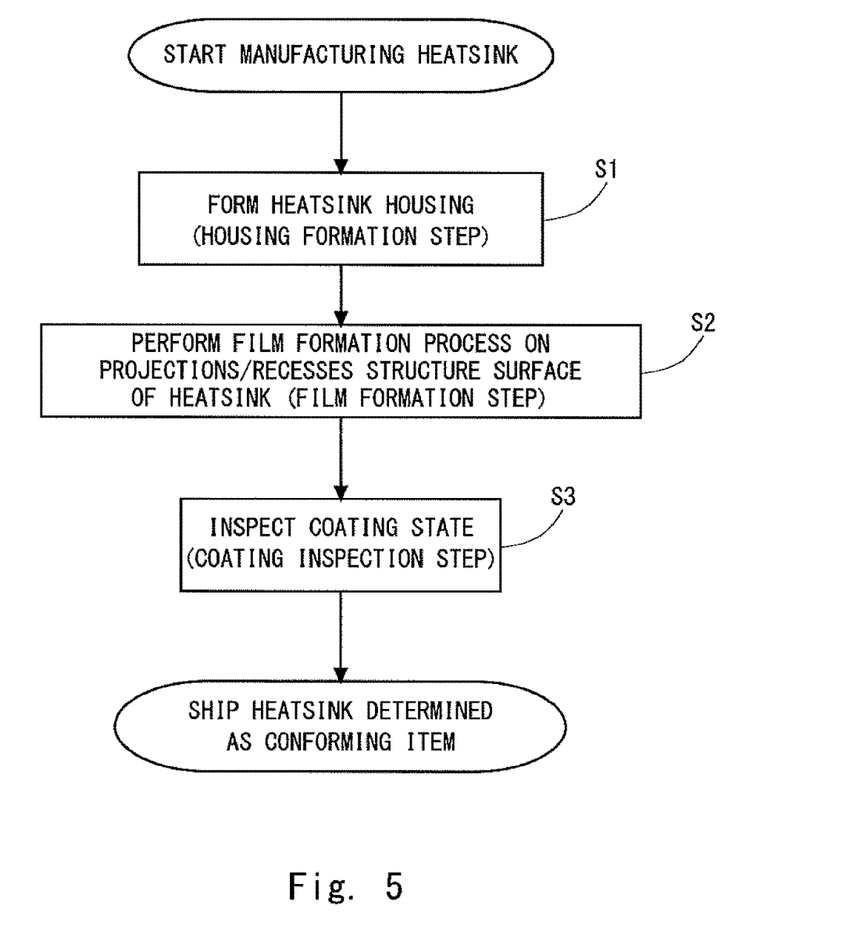
FIG. 5 is a flowchart for explaining a manufacturing method for a heatsink according to the first embodiment.

Next, a manufacturing method for a heatsink according to the first embodiment is explained. Therefore, FIG. 5 shows a flowchart for explaining a manufacturing method for a heatsink according to the first embodiment. As shown in FIG. 5, in the manufacturing method for a heatsink according to the first embodiment, firstly, a housing formation step of forming a heatsink housing is performed (step S1). In this housing formation step, a heatsink housing including the base part 10, which is a part that comes into contact with a heat-generating element, and the fins 11a to 11c disposed in the base part so as to protrude therefrom is manufactured by casting.

Next, a film formation step of performing a film formation process on projections and recesses of a heatsink is performed (step S2). In this film formation step, a heatsink is formed by coating a surface of a heatsink housing with a coating so that at least fins 11a to 11c are coated with the coating.

Next, a coating inspection step of inspecting a state of the coating formed in the step S2 is performed (step S3). This coating inspection step includes a plurality of steps (which are described later). Then, the manufacturing process for heatsinks are completed by shipping heatsinks that are determined to be conforming items (or good products) in the coating inspection step.

Note that in the manufacturing method for a heatsink according to the first embodiment, the film formation step and the coating inspection step (in particular, a later-described measurement preparation step and a measurement step) are performed before the temperature of the heatsink housing that has been raised by the casting performed in the housing formation step is lowered to or below a predefined measurement-performable temperature. In this way, the coating inspection step can be completed without reheating the heatsink and hence the time required for the manufacturing process can be reduced.

Figure 6:
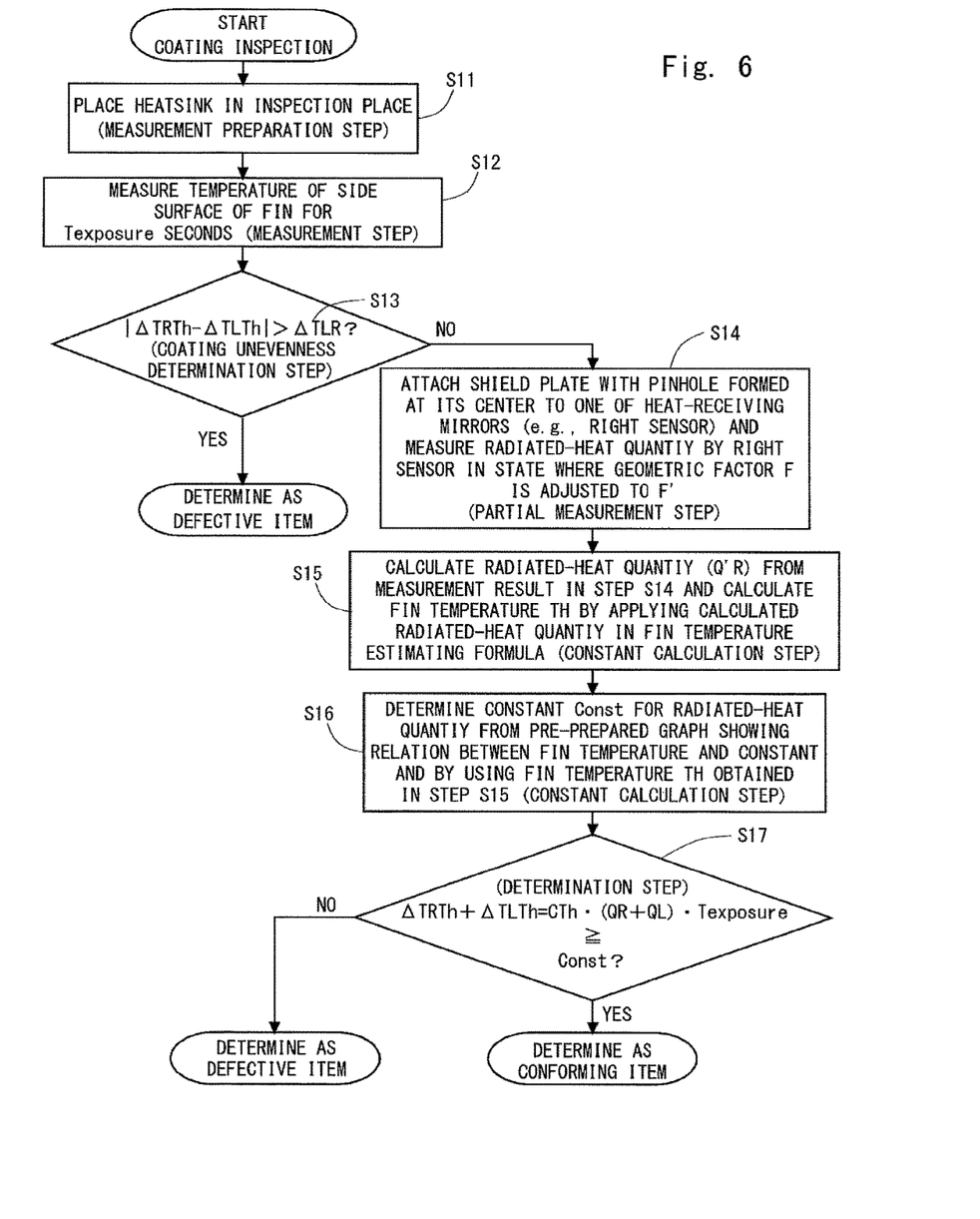
FIG. 6 is a flowchart for explaining an inspection method for a heatsink according to the first embodiment.

The coating inspection step is explained hereinafter in detail. Therefore, FIG. 6 shows a flowchart for explaining an inspection method for a heatsink (e.g., a coating inspection step) according to the first embodiment. As shown in FIG. 6, in the inspection method for a heatsink according to the first embodiment, firstly, a measurement preparation step of placing a heatsink to be inspected in an inspection place (step S11). More specifically, in the measurement preparation step, a heatsink is placed in a place where radiated-heat quantities can be measured by the first and second thermal sensors each of which is disposed in a different place in a state where a heat-receiving axis connecting the bottom of the concave shape of the heat-receiving surface with the temperature sensor is inclined from the direction in which the fins protrude by a predetermined angle.

Next, in the inspection method for a heatsink according to the first embodiment, a measurement step of measuring the temperature of side surface of the fin for Texposure seconds (e.g., one second corresponding to the unit time) is performed (step S12). In this measurement step, the radiated-heat quantities of the fin are measured by using the thermal sensors 12 and 13 and hence first and second radiated-heat quantities (e.g., temperature variations $\Delta TRTh$ and $\Delta TLTh$, respectively) are acquired from the thermal sensors 12 and 13, respectively. Note that in this measurement step, temperature information TR and TL are obtained from the thermistors 12b and 13b, respectively. Therefore, in the coating inspection system 1 according to the first embodiment, the temperature variations $\Delta TRTh$ and $\Delta TLTh$ are obtained by calculation using the temperature information performed in the arithmetic unit 15.

More specifically, in the arithmetic unit 15, temperature variations $\Delta TRTh$ (=TRTh_ini-TR) and $\Delta TLTh$ (=TLTh_ini-TL) of the thermistors 12b and 13b are calculated from differences between initial temperatures TRTh_ini and TLTh_ini of the thermistors and the acquired temperature information FR and TL.

Further, in the inspection method for a heatsink according to the first embodiment, a determination step of determining that the coating state of the coating is fine when the total value of the first and second radiated-heat quantities (e.g., heat quantities QR and QL, respectively) is larger than a predetermined range defined in advance is performed (step S17). However, since a constant that is used to determine the predetermined range used in the determination step has) not been determined yet, processes in steps S14 to S16 are performed. Further, in the inspection method for a heatsink according to the first embodiment, coating unevenness of the coating is determined before performing processes in steps S13 to S17. By doing so, products that are defective due to coating unevenness are fount at an early stage, so that the time required for the inspection step for a large number of heatsinks is reduced.

In the coating unevenness determination step (step S13) in the inspection method for a heatsink according to the first embodiment, the coating state of the coating is determined as defective when a difference between the temperature variations ΔTRTh and ΔTLTh has a value outside a predefined coating unevenness determination range.

Note that a relation between the temperature variation ΔTRTh and the heat quantity QR is expressed by Expression (1). In Expression (1): CTh is the heat capacity of the thermistor; Texposure is a measurement time; QR is a heat quantity [W] per unit time received by the thermistor 12b.

[Expression 1]

$$\Delta TRTh = CTh \cdot QR \cdot Texposure \quad (1)$$

Further, a relation between the temperature variation ΔTLTh and the heat quantity QL is expressed by Expression (2). In Expression (2): CTh is the heat capacity of the thermistor; Texposure is a measurement time; QR is a heat quantity [W] per unit time received by the thermistor 13b.

[Expression 2]

$$\Delta TLTh = CTh \cdot QL \cdot Texposure \quad (2)$$

From Expressions (1) and (2), it is understood that, because the heat capacity CTh of the thermistor and the measurement time Texposure are constant, the difference between the heat quantities QR and QL results from the difference between the temperature variations ΔTRTh and ΔTLTh. Therefore, in the example shown in FIG. 6, the presence/absence of coating unevenness is determined based on whether or not the absolute value of the difference between) the temperature variations ΔTRTh and ΔTLTh exceeds a coating unevenness determination range ΔTRL. When the coating is uniformly formed, the temperature variations ΔTRTh and ΔTLTh have the same value as each other. However, there are cases in which even when the coating is uniformly formed, these two values are not equal to each other due to a measurement error or the like. Therefore, the coating unevenness determination range ΔTRL is preferably a value including (or tolerating) measurement variations caused by a measurement error of the thermal sensor or the like. Further, in the manufacturing method for a heatsink according to the first embodiment, it is possible to swiftly perform the coating unevenness determination process by determining the presence/absence of coating unevenness based on the difference between the two temperature variations without calculating the heat quantity.

Note that the coating unevenness determination step can be performed because the coating inspection system 1 has a configuration in which two thermal sensors are arranged so that the areas of the fin measured by the two thermal sensors are equal to each other.

The coating unevenness determination step is further explained hereinafter in detail. Firstly, the heat quantity radiated from the right side surface of the fin is expressed by Expression (3). Further, the heat quantity radiated from the left side surface of the fin is expressed by Expression (4). In Expressions (3) and (4): F is a geometric factor from the heatsink housing to the thermistor; εR is an emissivity on a local area dS on the right side surface of the fin; S is an area on the surface to be inspected; εL is an emissivity on a local area dS on the left side surface of the fin; εTh is an emissivity of the thermistor; σ is the Stefan-Boltzmann constant; TH is the temperature of the fin of the heatsink housing; TRTh is the temperature of the thermistor 12b of the thermistor 12; and TLTh is the temperature of the thermistor 13b of the thermistor 13.

[Expression 3]

$$QR[W] = F \left| \frac{\int \varepsilon_R dS}{S} \right| \varepsilon_{Th} \sigma (TH^4 - THTh^4) \quad (3)$$

[Expression 4]

$$QL[W] = F \left| \frac{\int \varepsilon_L dS}{S} \right| \varepsilon_{Th} \sigma (TH^4 - TLTh^4) \quad (4)$$

Further, it can be understood that based on the fact that the heat capacity CTh of the thermistor and the measurement time Texposure are constant in Expressions (1) and (2), the difference between the temperature variations ΔTRTh and ΔTLTh results from the difference between the heat quantities QR and QL. Next, it can be understood that based on the fact that the geometric factor F, the emissivity εTh of the thermistor, and the Stefan-Boltzmann constant σ are constants, and the temperature TH of the fin is the same in Expressions (3) and (4), the difference between the heat quantities QR and QL results from the difference between the emissivity εR on the right side surface of the fin and the emissivity εL on the left side surface of the fin. That is, it can be understood that the difference between the temperature variations ΔTRTh and ΔTLTh results from the coating unevenness of the coatings on the left and right side surfaces of the fin. Based on the above-described matters, in the coating unevenness determination step in the step S13, a heatsink in which the above-described coating unevenness occurs is determined to be a defective item (or a defective product). On the other hand, for a heatsink that is determined to be a conforming item in the coating unevenness determination step in the step S13, processes in the step S14 and subsequent steps are performed.

In the step S14, a partial measurement step using one of the thermal sensors 12 and 13 (e.g., the thermal sensor 12) is performed. Specifically, in this partial measurement step, the third radiated-heat quantity (e.g., a temperature variation ΔTRTh') is measured in a state in which a heat-shield plate that restricts the quantity of incident heat rays (infrared rays) on the thermal sensor 12 to a predetermined range is disposed in front of the thermal sensor 12. In this partial measurement step, the rotation plate 20 explained above with reference to FIG. 4 is rotated and the partial opening 22 is thereby disposed in front of the thermal sensor 12. As a result, the geometric factor F is changed to a geometric factor F'. That is, the size of the partial opening 22 is preferably set to a size with which the geometric factor F is changed to the geometric factor F'.

Next, in steps S15 and S16, a constant calculation step of calculating a constant Const that is used to determine the predetermined range used in the step S17 from the temperature variation ΔTRTh' is performed. In the step S15, the temperature TH of the fin (hereinafter referred to as a "fin temperature TH") is calculated. In this calculation of the fin temperature TH, firstly, a heat quantity Q'R is calculated by substituting the temperature variation ΔTRTh' for the left-hand side of Expression (1). Further, a relation between the calculated heat quantity Q'R and the fin embodiment TH can be expressed by a fin temperature estimating formula expressed as Expression (5). In Expression (5): F' is a geometric factor in a measurement system in the step S14; σ is the Stefan-Boltzmann constant; π is the circular constant; and r is a radius of the partial opening 22.

[Expression 5]

$$Q'R[W]=F'\sigma(TH^4-TRTh^4)\pi r^2 \quad (5)$$

Since all the values except for the fin temperature TH are known in this Expression (5), the arithmetic unit 15 calculates the fin temperature TH by using Expression (5) and these known values.

Figure 7:
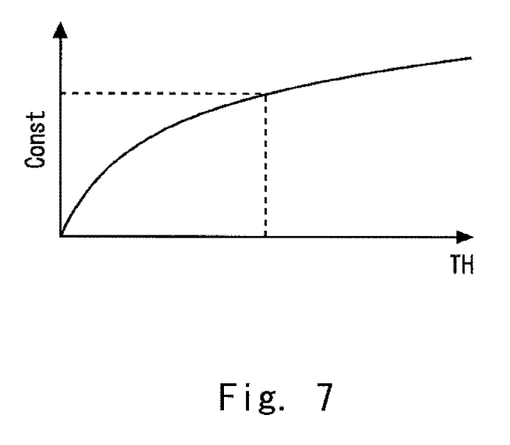
FIG. 7 is a diagram for explaining an example of a graph used in a constant calculation step performed during an inspection procedure for a heatsink according to the first embodiment.

Next, in the step S16, the constant Const for the radiated-heat quantity is determined from a pre-prepared graph showing a relation between the fin temperature and the constant Const by using the fin temperature TH obtained in the step S15. Here, FIG. 7 shows a diagram for explaining an example of the graph used in the constant calculation step performed during the inspection procedure for a heatsink according to the first embodiment. The graph shown in FIG. 7 is obtained, for example, as a result of measurement of the fin temperature TH and the constant Const carried out in a trial manufacturing stage of a heatsink. Further, as shown in FIG. 7, the fin temperature TH and the constant Const have a relation expressed as a certain curved line. Further, the data of this graph is stored in a memory or the like disposed in the arithmetic unit 15. The arithmetic unit 15 determines the constant Const by using the graph shown in FIG. 7.

Next, in the inspection method for a heatsink according to the first embodiment, a determination step of determining that the coating state of the coating is fine when the total value of the radiated-heat quantities ΔTRTh and ΔTLTh acquired in the step S11 is larger than the predetermined range defined in advance is performed (step S17). In this determination step, the aforementioned predetermined range is determined by using the constant Const determined in the step S16. Then, when Expression (6) is satisfied, the heatsink is determined as a conforming item, whereas when Expression (6) is not satisfied, the heatsink is determined as a defective item.

[Expression 6]

$$\Delta TRTh+\Delta TLTh=CTh\cdot(QR+QL)\cdot Texposure \geq Const \quad (6)$$

As explained above, in the inspection method for a heatsink according to the first embodiment, radiant heat radiated from the fin is acquired from a wide area of the fin by acquiring the radiated-heat quantities from different places on the side surfaces of the fin (e.g., the left-side surface and the right-side surface of the fin) of the heatsink. As a result, in the inspection method for a heatsink according to the first embodiment, it is possible to accurately inspect the coating state on the side surface of the fin.

Further, in the inspection method for a heatsink according to the first embodiment, a pass/fail determination based on coating unevenness of the coating is performed by measuring radiated-heat quantities from side surfaces having the same area (i.e., the same size) of the fin by using two thermal sensors and comparing these two radiated-heat quantities with each other. In this way, in the inspection method for a heatsink according to the first embodiment, it is possible to detect defective heatsinks before performing the pass/fail determination of the coating based on the fin temperature TH, which requires a long time, and thereby to reduce the time required to inspect a large number of heatsinks.

Further, in the inspection method for a heatsink according to the first embodiment, fins of a heatsink to be inspected are formed so as to protrude in the vertical direction with respect to the base part 10. In such a heatsink, it is possible to equally expose the side surfaces of the fin to two thermal sensors by arranging the thermal sensors 12 and 13 on the left and right side of the fin. That is, in the inspection method for a heatsink according to the first embodiment, it is possible to improve the measurement accuracy, in particular, for a heatsink in which fins of the heatsink are formed so as to protrude in the vertical direction with respect to the base part 10.

Further, in the inspection method for a heatsink according to the first embodiment, the angle between the center line of the heatsink and the heat-concentrating axis of the thermal sensor is adjusted to an angle at which the area of the side surface of the fin that is exposed to the heat-receiving surface of the thermal sensor is maximized. As a result, in the inspection method for a heatsink according to the first embodiment, it is possible to acquire the radiated-heat quantity from the maximum measurement-performable area on the side surface of the fin and thereby to improve the measurement accuracy.

Further, in the inspection method for a heatsink according to the first embodiment, the heat-receiving surface of each thermal sensor has an area that can collectively receive heat rays (infrared rays) radiated from all the fins provided in the heatsink. As a result, in the inspection method for a heatsink according to the first embodiment, it is possible to acquire the radiated-heat quantity from the maximum area on the side surface of the fin at one measurement timing without scanning the measurement place. That is, in the inspection method for a heatsink according to the first embodiment, it is possible to reduce the inspection time.

Further, the inspection method for a heatsink according to the first embodiment includes a partial measurement step of measuring the third radiated-heat quantity (e.g., a temperature variation ΔTRTh') in a state in which a heat-shield plate having a partial opening is disposed in front of one of the thermal sensors (e.g., the thermal sensor 12) (e.g., a state in which the partial opening 22 is disposed in front of the thermal sensor 12), and a constant calculation step of calculating a constant Const that is used to determine the predetermined range from the third radiated-heat quantity. As a result, in the inspection method for a heatsink according to the first embodiment, it is possible to determine the constant Const even when the temperature TH of the heatsink is unknown at the point when the coating inspection is performed. In particular, in the inspection method for a heatsink according to the first embodiment, since a coating application step and a coating inspection step are performed by using remaining heat of a casting step in which a heatsink housing is formed, there are variations in the heatsink temperature TH at the point when the coating inspection is performed. Therefore, estimating the temperature TH of the heatsink in the coating inspection step and changing the constant Const based on this estimated temperature have a considerable effect for the improvement of the inspection accuracy.

Further, in the inspection method for a heatsink according to the first embodiment, the coating application step and the coating inspection step are performed by using remaining heat of the casting step in which the heatsink housing is formed. As a result, in the inspection method for a heatsink according to the first embodiment, there is no need to reheat the heatsink for the inspection, thus making it possible to reduce the inspection time.

Second Embodiment

In a second embodiment, a coating inspection system 2, which is a modified example of the coating inspection system 1 according to the first embodiment, is explained. Note that in the explanation of the second embodiment, the same symbols as those of the first embodiment are assigned to the same components as those of the first embodiment and their explanations are omitted.

Figure 8:
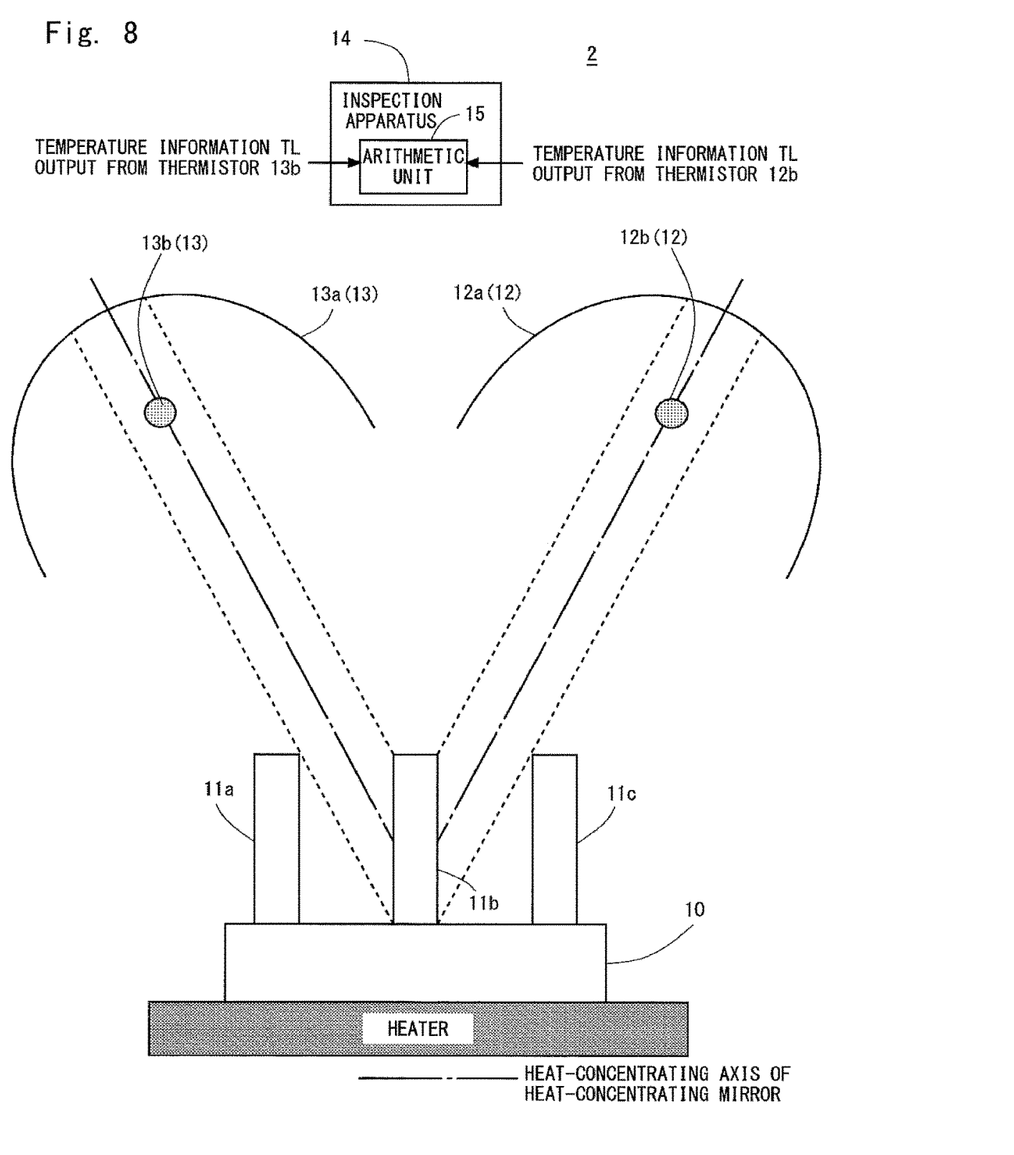
FIG. 8 is a schematic diagram for explaining a configuration of a coating inspection system according to a second embodiment.

FIG. 8 shows a schematic diagram for explaining a configuration of the coating inspection system 2 according to the second embodiment. As shown in FIG. 8, in the coating inspection system 2 according to the second embodiment, a heater is provided below a heatsink to be inspected (e.g., on a surface of the base part 10 that comes into contact with a heat-generating element). This heater is used to adjust the temperature of the heatsink to a predefined temperature TH' in a coating inspection step.

A manufacturing method for a heatsink according to the second embodiment differs from the manufacturing method for a heatsink according to the first embodiment in that the heater is used in the coating inspection step. Therefore, FIG. 9 is a flowchart for explaining an inspection method for a heatsink according to the second embodiment.

Figure 9:
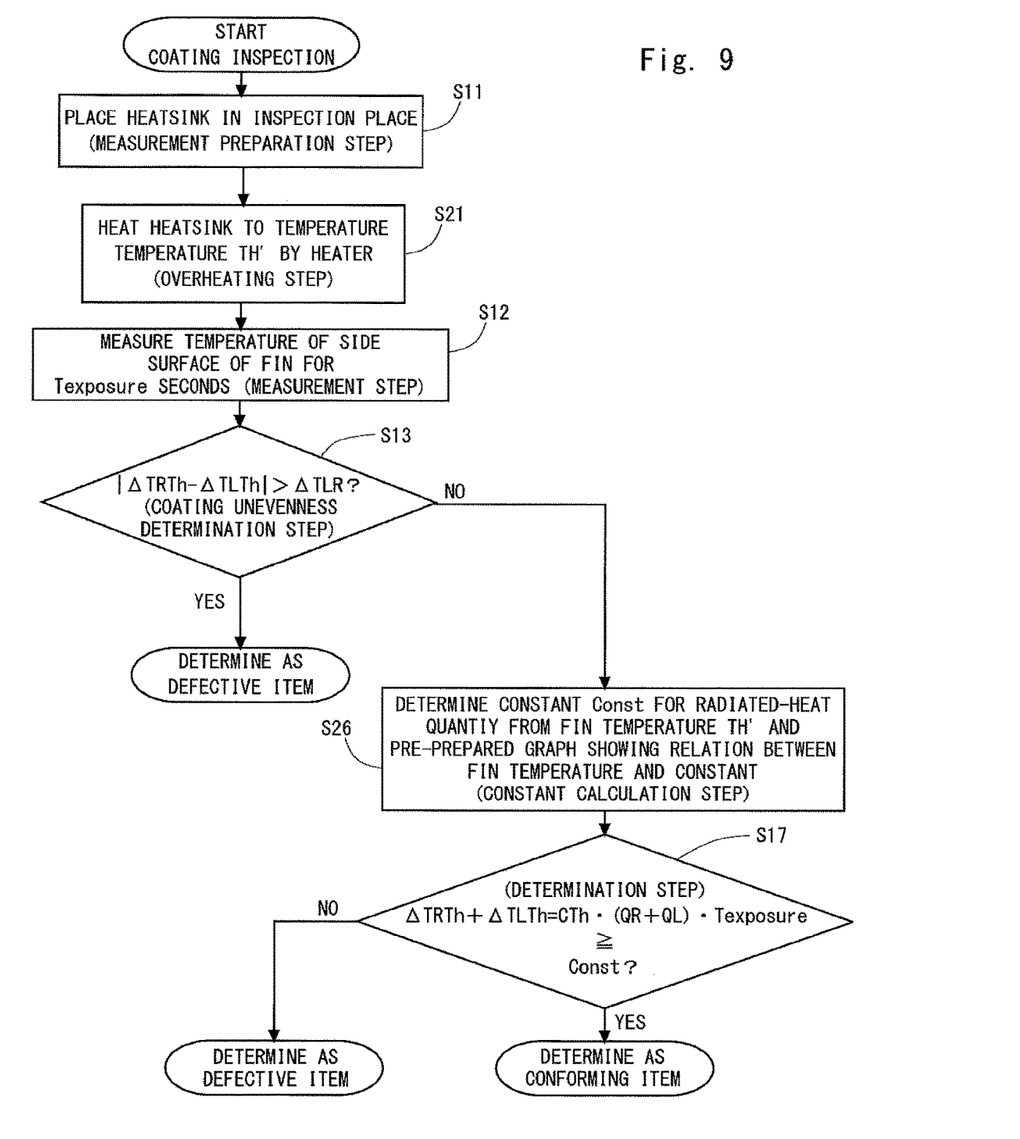
FIG. 9 is a flowchart for explaining an inspection method for a heatsink according to the second embodiment.

As shown in FIG. 9, in the inspection method for a heatsink according to the second embodiment, an overheating step of overheating a heatsink to a temperature TH' by using the heater is preformed (step S21) between the measurement preparation step in the step S11 and the measurement step in the step S12. That is, in the coating inspection step according to the second embodiment, the radiated-heat quantity of the fin is measured in a state in which the temperature of the fin has become the temperature TH'.

Further, as shown in FIG. 9, in the inspection method for a heatsink according to the second embodiment, since it is already known that the fin temperature is the temperature TH', the process for acquiring the fin temperature in the steps S14 and S15 in the inspection method for a heatsink according to the first embodiment can be omitted. Further, in the inspection method for a heatsink according to the second embodiment, a step S26 is performed in place of the step S16 of the first embodiment. The step S26 is a constant calculation step. In this step, a constant Const is obtained by using the known fin temperature TH' and the graph shown in FIG. 7.

As explained above, in the inspection method for a heatsink according to the second embodiment, the constant Const is derived by adjusting the fin temperature to the temperature TH' by using the heater without actually measuring the fin temperature. As a result, in the inspection method for a heatsink according to the second embodiment, the measurement and calculation for estimating the fin temperature can be omitted, thus making it possible to reduce the inspection time.

Further, in the inspection method for a heatsink according to the second embodiment, since the fin temperature is adjusted to the predefined temperature, the constant Const can be calculated without being affected by the error in the measurement that would otherwise need to be performed to estimate the fin temperature. That is, in the inspection method for a heatsink according to the second embodiment, it is possible to reduce the effect of the error in the measurement that would otherwise need to be performed to estimate the fin temperature and thereby to improve the inspection accuracy.

Note that even in the manufacturing method for a heatsink according to the second embodiment, when the coating inspection step is performed, the heatsink may have heat that is generated by the casting process performed to manufacture the heatsink housing. Even when there is the remaining heat as described above, the inspection accuracy can be improved by stabilizing the fin temperature by using the heater when the coating inspection step is performed.

From the invention thus described, it will be obvious that the embodiments of the invention may be varied in many ways. Such variations are not to be regarded as a departure from the spirit and scope of the invention, and all such modifications as would be obvious to one skilled in the art are intended for inclusion within the scope of the following claims.

What is claimed is:

1. An inspection method for a heatsink comprising a base part and a fin disposed in the base part so as to protrude therefrom, the base part being a part that comes into contact with a heat-generating element, the fin being coated with a coating, the inspection method comprising:

a measurement preparation step of placing the heatsink in a place where radiated-heat quantities can be measured by first and second thermal sensors, each of the first and second thermal sensors comprising a temperature sensor and a heat-concentrating mirror with a heat-receiving surface curved in a concave shape, the heat-concentrating mirror being configured to concentrate received heat onto the temperature sensor based on the concave shape, the first and second thermal sensors being disposed in different places in a state where a heat-receiving axis connecting a bottom of the concave shape of the heat-receiving surface with the temperature sensor is inclined from a direction in which the fin protrudes by a predetermined angle;

a measurement step of measuring the radiated-heat quantity of the fin and acquiring first and second radiated-heat quantities from the first and second thermal sensors, respectively; and a determination step of determining that a coating state of the coating is fine when a total value of the first and second radiated-heat quantities is larger than a predetermined range defined in advance.

2. The inspection method for a heatsink according to claim 1, wherein the first and second thermal sensors are disposed in places where exposed areas of the fin that can be observed from the thermal sensors are equal to each other, and the determination step further comprises a coating unevenness determination step of determining that a coating state of the coating is defective when a difference between the first and second radiated-heat quantities has a value outside a predefined coating unevenness determination range.

3. The inspection method for a heatsink according to claim 1, wherein the fin is formed so as to protrude in a vertical direction with respect to a heat-radiating surface provided in a place opposed to a heat-generating surface, the heat-generating surface being one of surfaces of the base part that is in contact with the heat-generating element, the first and second thermal sensors are arranged in left-right symmetrical places with respect to a center line of the heatsink, the center line being defined in the vertical direction with respect to the base part of the heatsink, and the inspection method further comprises a coating unevenness determination step of determining that a coating state of the coating is defective when a difference between the first and second radiated-heat quantities has a value outside a predefined coating unevenness determination range.

4. The inspection method for a heatsink according to claim 1, wherein the predetermined angle is an angle at which an area of the side surface of the fin that is exposed to the heat-receiving surface is maximized.

5. The inspection method for a heatsink according to claim 1, wherein each of the heat-receiving surfaces of the first and second thermal sensors have an area that can collectively receive heat rays emitted from all the fins provided in the heatsink.

6. The inspection method for a heatsink according to claim 1, wherein
the first thermal sensor comprises a heat-shield plate disposed in front of the heat-receiving surface, the heat-shield plate being configured to restrict an area on the heat-receiving surface on which heat rays are incident to a predetermined area, and
the inspection method further comprises:
a partial measurement step of measuring the third radiated-heat quantity in a state where the heat-shield plate is disposed in front of the first thermal sensor, and
a constant calculation step of calculating a constant from the third radiated-heat quantity, the constant being used to define the predetermined range.

7. The inspection method for a heatsink according to claim 1, further comprising:
an overheating step of overheating the heatsink by using a heater, the heater being configured to raise the temperature of the heatsink to a predefined measurement temperature before the measurement step, and
a constant calculation step of calculating a constant from the measurement temperature, the constant being used to define the predetermined range used in the determination step.

8. A manufacturing method for a heatsink, comprising:
a housing formation step of manufacturing a heatsink housing by casting, the heatsink housing comprising a base part and a fin disposed in the base part so as to protrude therefrom, the base part being a part that comes into contact with a heat-generating element;
a film formation step of forming a heatsink by coating a surface of the heatsink housing with a coating so that at least the fin is covered by the coating;
a measurement preparation step of placing the heatsink housing, which has undergone the film formation step, in a place where radiated-heat quantities can be measured by first and second thermal sensors, each of the first and second thermal sensors comprising a temperature sensor and a heat-concentrating mirror with a heat-receiving surface curved in a concave shape, the heat-concentrating mirror being configured to concentrate received heat onto the temperature sensor based on the concave shape, the first and second thermal sensors being disposed in different places in a state where a center line connecting a bottom of the concave shape of the heat-receiving surface with the temperature sensor is inclined from a direction in which the fin protrudes by a predetermined angle;
a measurement step of measuring the radiated-heat quantity of the fin and acquiring first and second radiated-heat quantities measured by the first and second thermal sensors, respectively; and
a determination step of determining that a coating state of the coating is fine when a total value of the first and second radiated-heat quantities is larger than a predetermined range defined in advance.

9. The manufacturing method for a heatsink according to claim 8, wherein the film formation step, the measurement preparation step, and the measurement step are performed before the temperature of the heatsink housing that has been raised by the casting performed in the housing formation step is lowered to or below a predefined measurement-performable temperature.

* * * * *